United States Patent
Bieberich et al.

(10) Patent No.: US 10,842,785 B2
(45) Date of Patent: *Nov. 24, 2020

(54) PIM KINASE INHIBITORS IN COMBINATION WITH RNA SPLICING MODULATORS/INHIBITORS FOR TREATMENT OF CANCERS

(71) Applicant: UNIVERSITY OF MARYLAND, BALTIMORE COUNTY, Baltimore, MD (US)

(72) Inventors: Charles J. Bieberich, Brookeville, MD (US); Xiang Li, Baltimore, MD (US); Tejashree Joglekar, Savage, MD (US)

(73) Assignee: THE UNIVERSITY OF MARYLAND, BALTIMORE COUNTY, Baltimore, MD (US)

(*) Notice: Subject to any disclaimer, the term of this patent is extended or adjusted under 35 U.S.C. 154(b) by 0 days.

This patent is subject to a terminal disclaimer.

(21) Appl. No.: 16/598,536

(22) Filed: Oct. 10, 2019

(65) Prior Publication Data
US 2020/0046689 A1 Feb. 13, 2020

Related U.S. Application Data

(62) Division of application No. 16/082,325, filed as application No. PCT/US2017/023546 on Mar. 22, 2017.

(60) Provisional application No. 62/313,289, filed on Mar. 25, 2016.

(51) Int. Cl.
| | |
|---|---|
| *A61K 31/454* | (2006.01) |
| *A61K 45/06* | (2006.01) |
| *A61K 31/365* | (2006.01) |
| *A61K 31/437* | (2006.01) |
| *A61K 31/453* | (2006.01) |
| *A61K 31/351* | (2006.01) |
| *A61K 31/506* | (2006.01) |
| *A61K 31/4412* | (2006.01) |
| *A61K 31/426* | (2006.01) |
| *A61K 31/165* | (2006.01) |
| *A61K 31/551* | (2006.01) |
| *A61K 31/5025* | (2006.01) |
| *A61P 35/00* | (2006.01) |
| *G01N 33/50* | (2006.01) |

(52) U.S. Cl.
CPC .......... *A61K 31/454* (2013.01); *A61K 31/165* (2013.01); *A61K 31/351* (2013.01); *A61K 31/365* (2013.01); *A61K 31/426* (2013.01); *A61K 31/437* (2013.01); *A61K 31/4412* (2013.01); *A61K 31/453* (2013.01); *A61K 31/506* (2013.01); *A61K 31/5025* (2013.01); *A61K 31/551* (2013.01); *A61K 45/06* (2013.01); *A61P 35/00* (2018.01); *G01N 33/5011* (2013.01)

(58) Field of Classification Search
CPC .............................. A61K 31/454; A61P 35/00
See application file for complete search history.

(56) References Cited

U.S. PATENT DOCUMENTS

| 7,368,258 B1 | 5/2008 | Bieberich et al. |
| 7,750,007 B2 | 7/2010 | Bearss et al. |
| 10,525,047 B2* | 1/2020 | Bieberich ............ A61K 31/365 |
| 2012/0208815 A1 | 8/2012 | Burger et al. |

FOREIGN PATENT DOCUMENTS

| JP | 2014183784 A | 10/2014 |
| WO | WO2009064486 A2 | 5/2009 |
| WO | WO2012129338 A1 | 9/2012 |
| WO | WO2012145617 A2 | 10/2012 |
| WO | WO2012148775 A1 | 11/2012 |
| WO | WO2013130660 A1 | 9/2013 |
| WO | WO2014022752 A1 | 2/2014 |
| WO | WO2014031360 A1 | 2/2014 |
| WO | WO2015019320 A1 | 2/2015 |

OTHER PUBLICATIONS

Chen, L.S. et al. Mechanisms of cytotoxicity to Pim kinase inhibitor, SGI-1776, in acute myeloid leukemia, *Blood*, 2011, 118(3):693-702 (abstract).

Kirschner, A.N. et al. "PIM kinase inhibitor AZD1208 for treatment of MYC-driven prostate cancer", *J Natl Cancer Inst*, 2014, 107(2) (abstract).

Lin, Y.W. et al. "A small molecule inhibitor of Pim protein kinases blocks the growth of precursor T-cell lymphoblastic leukemia/lymphoma", *Blood*, 2010 115(4): 824-33 (abstract).

Meja, K. et al. "PIM and AKT kinase inhibitors show synergistic cytotoxicity in acute myeloid leukemia that is associated with convergence on mTOR and MCL1 pathways", *British Journal of Haematology*, 2014, vol. 167, pp. 69-79.

Mizui, Y. et al. "Pladienolides, new substances from culture of Streptomyces platensis Mer-11107. III. In vitro and in vivo antitumor activities", *J Antibot (Tokoyo)*, 2004, 57(3):188-96 (abstract).

Nakajima, H. et al. "New antitumor substances, FR901463, FR901464 and FR901465. II. Activities against experimental tumors in mice and mechanism of action", *J Antibiot (Tokyo)*, 1996, 49(12):1204-11 (abstract).

(Continued)

*Primary Examiner* — Rei Tsang Shiao
(74) *Attorney, Agent, or Firm* — Marianne Fuierer; Olive Law Group, PLLC (57) ABSTRACT

The present invention provides for a method of treating cancer and/or reducing proliferation of cancer cells, the method comprising administering to a subject in need of such treatment a composition comprising a PIM kinase inhibitor that exhibits changes of mRNA splicing in combination with a compound that modulates/inhibits activity of an RNA splicing factor protein. Further, changes in splicing of mRNAs and phosphorylation of RNA splicing factors can be used as biomarkers for patient responsiveness to anti-PIM treatment and also suggest effective combinatorial therapies, including synergistic combination.

6 Claims, 8 Drawing Sheets

(56) References Cited

OTHER PUBLICATIONS

O'Brien, K. et al. "The biflavonoid isoginkgetin is a general inhibitor of Pre-mRNA splicing", *J Biol Chem*, 2008, 283(48): 33147-54 (abstract).

Rogriguez, D.A. et al. "BH3-only proteins are part of a regulatory network that control the sustained signaling of the unfolded protein response sensor IRE1alpha", *The EMBO Journal*, 2012, vol. 31, No. 10, pp. 2322-2335.

Sato, M. et al. "High antitumor activity of pladienolide B and its derivative in gastric cancer", *Cancer Sci*, 2014, 105(1): 110-6 (abstract).

Shou, J-W. et al. "Isolation of novel bioflavonoids from Cardiocrinum gigantem seeds and characterization of their antitussive activities", *CAS*, 2018, 170:394479.

Siqueira, P.R. et al. "Potential Antileukemia Effect and Structural Analyses of SRPK Inhibition by N-(2-(Piperidin-1-yl)-5-(Trifluoromethyl)Phenyl) Isonicotinamide (SRPIN340)", *PLoS one*, 2015, 10(8):e0134882 (abstract).

Song, J. H. et al. "Pim kinase inhibitors sensitize prostate cancer cells to apoptosis triggered by Bcl-2 family inhibitor ABT-737", *Cancer Research*, 2012, vol. 72, No. 1, pgs. 294-303.

Viqushin, D.M. et al. "Trichostatin A is a histone deacetylase inhibitor with potent antitumor activity against breast cancer in vivo", *Clin Cancer Res*, 2001, 7(4): 971-6 (abstract).

\* cited by examiner

HTA2.0 Array analysis identifies >10000 splicing events regulated by Pim activity

Total changes: 5572 genes and exon rows: 10170

| Mode | Genes | Exon rows |
|---|---|---|
| Exon Skipping | 1086 | 1851 |
| Mutually exclusive exons | 2 | 5 |
| Alternative 5' Donor | 616 | 797 |
| Alternative 3' acceptor | 612 | 767 |
| Intron retentions | 184 | 276 |

Figure 4 B

Exon skipping

Mutually exclusive exons

Alternative 5' donor sites

Alternative 3' acceptor sites

Intron retention

PIM KINASE INHIBITORS IN COMBINATION WITH RNA SPLICING MODULATORS/INHIBITORS FOR TREATMENT OF CANCERS

CROSS-REFERENCE TO RELATED APPLICATION

This application is a divisional application claiming priority to U.S. patent application Ser. No. 16/082,325 file on Sep. 5, 2018, now U.S. patent application Ser. No. 10,525,047, which was filed under the provisions of 35 U.S.C. § 371 and claimed priority of International Patent Application No. PCT/US2017/023546 filed on Mar. 22, 2017 which in turn claimed priority to U.S. Provisional Patent Application No. 62/313,289 filed on Mar. 25, 2016, the contents of which is hereby incorporated by reference herein for all purposes.

STATEMENT REGARDING FEDERALLY SPONSORED RESEARCH

This invention was made with government support under Grant Number NIH 5R21CA155568-02 awarded by the National Institutes of Health. The government has certain rights in the invention.

BACKGROUND OF THE INVENTION

Field of the Invention

The present invention relates to the treatment of a cancer in a patient through administration of a PIM kinase inhibitor in combination with an RNA splicing modulator/inhibitor.

Related Art

In the treatment of human diseases, resistance to chemotherapeutic agents is a growing problem. The situation is particularly acute in the treatment of malignancies: rapid cell division rates combined with genomic instability provides fertile ground for the emergence of, and positive selection for, mutations that confer drug resistance. One potential solution to this intransigent problem is to combine therapeutic agents to achieve tumor control. For example, combinations of targeted agents, or combinations of targeted agents and conventional chemotherapies can be envisaged. The difficulty in taking this approach lies in determining which combinations of two or more agents will be effective.

Kinases are enzymes that are major drivers of oncogenic processes in the cell. Virtually all cancer cases involve over-activation of one or more kinases. Kinase inhibition has emerged as a major therapeutic entry point for cancer treatment. The paradigm for this approach is the small molecule BCR-ABL kinase inhibitor Gleevec. While Gleevec has met with phenomenal clinical and commercial success, few other kinase inhibitors are clinically available, due, in large measure, to their lack of efficacy in vivo at their clinically applicable doses. One potential solution to this problem is to combine kinase inhibition with either another targeted drug, or a conventional chemotherapeutic agent. Currently, there is little information available to rationally guide the choice of agents to combine with kinase inhibitors. This lack of information stems from the fact that, for most kinases, there is a limited view of the downstream pathways that they regulate.

Pro-growth kinase up-regulation is a common feature of nearly all cancers and a major target for therapeutic intervention. Proviral integration site for Moloney murine leukemia virus (PIM) kinases comprise a family of oncogenic kinases, which are deregulated in hematopoietic cancers including Acute Myeloid Leukemia (AML) as well as epithelial malignancies like prostate cancer. Several features of PIM kinases make them an excellent target for cancer therapy. PIM kinases are constitutively active and are dispensable for growth of most normal adult tissues.

However, to date, very few substrates have been identified for PIM kinases.

Thus, it would be advantageous to fully characterize the physiological roles of PIM kinases and with such discovery provide a new combination of effective therapies to treat cancer.

Additionally, such a discovery would provide a new and novel assay for determining the effectiveness of suspected PIM kinases inhibitors.

SUMMARY OF THE INVENTION

The present invention relates to the discovery that PIM kinases regulate mRNA splicing by phosphorylating mRNA splicing factors and causing cell proliferation inhibition. As such, a PIM kinase inhibitor can be combined with an RNA splicing modulator/inhibitor, which has the ability to modulate or change mRNA splicing, to inhibit proliferation of cancer cells.

In one aspect, the present invention provides for a method of treating cancer and/or reducing proliferation of cancer cells, the method comprising administering to a subject in need of such treatment a composition comprising a PIM kinase inhibitor that exhibits changes of mRNA splicing in combination with a compound that modulates and/or alters activity of an RNA splicing factor protein.

The PIM kinase inhibitor may include, but is not limited to SGI-1776 (N-[(1-methylpiperidin-4-yl)methyl]-3-[3-(trifluoromethoxy)phenyl]imidazo[1,2-b]pyridazin-6-amine), SMI-4a (5-[[3-(trifluoromethyl)phenyl]methylidene]-1,3-thiazolidine-2,4-dione), CX-6258 (E)-5-chloro-3-((5-(3-(4-methyl-1,4-diazepane-1-carbonyl)phenyl)furan-2-yl)methylene)indolin-2-one), LKB1 (N-[5-(4-cyanophenyl)-1H-pyrrolo[2,3-b]pyridin-3-yl]pyridine-3-carboxamide), AZD1208 ((5E)-5-[[2-[(3R)-3-aminopiperidin-1-yl]-3-phenylphenyl]methylidene]-1,3-thiazolidine-2,4-dione), PIM-1 Inhibitor 2 (4-[3-(4-chlorophenyl)-2,1-benzoxazol-5-yl]pyrimidin-2-amine), R8-T198 wt and TCS PIM-1 (6-(5-bromo-2-hydroxyphenyl)-2-oxo-4-phenyl-1,2-dihydropyridine-3-carbonitrile).

A compound that modulates or alters splicing activity of a RNA splicing factor may include but is not limited to a member selected from the group; a natural product of *Pseudomonas* sp. number 2663 (FR901464), natural products from *Streptomyces platensis* Mer-11107, pladienolide B (targets splicing factor 3B subunit 1 of the spliceosome, causing changes in splicing patterns), herboxidien, trichostatin, isoginkgetin and analogues thereof, 2-((7methoxy-4-methylquinazolin-2-yl)amino)-5,6-dimethylpyrimidin-4(3H)-one, and bovine papillomavirus type 1 (BPV-1) exonic splicing suppressor (ESS), N-[2-(1-Piperidinyl)-5-(trifluoromethyl)phenyl]-4-pyridinecarboxamide (SRPIN340).

RNA splicing factors that are affected by PIM kinase inhibitors include but not limited to:
  SRSF1_HUMAN Serine/arginine-rich splicing factor 1
    OS=*Homo sapiens* GN=SRSF1 PE=I1 SV=2;
  SRSF5_HUMAN Serine/arginine-rich splicing factor 5
    OS=*Homo sapiens* GN=SRSF5 PE=1 SV=1;

SRSF6_HUMAN Serine/arginine-rich splicing factor 6 OS=*Homo sapiens* GN=SRSF6 PE=I1 SV=2;

SRSF7_HUMAN Serine/arginine-rich splicing factor 7 OS=*Homo sapiens* GN=SRSF7 PE=1 SV=1;

SRS1O_HUMAN Serine/arginine-rich splicing factor 10 OS=*Homo sapiens* GN=SRSF10 PE=I1 SV=1;

U2AF1_HUMAN Splicing factor U2AF 35 kDa subunit OS=*Homo sapiens* GN=U2AF1 PE=$^{-1}$ SV=3;

CWC22_HUMAN Pre-mRNA-splicing factor CWC22 homolog OS=*Homo sapiens* GN=CWC22 PE=I1 SV=3;

SF3B2_HUMAN Splicing factor 3B subunit 2 OS=*Homo sapiens* GN=SF3B2 PE=1 SV=2;

SF01 HUMAN Splicing factor 1 OS=*Homo sapiens* GN=SF1 PE=1 SV=4;

SFR19 HUMAN Splicing factor, arginine/serine-rich 19 OS=*Homo sapiens* GN=SCAF1 PE=I1 SV=3;

PR38A_HUMAN Pre-mRNA-splicing factor 38A OS=*Homo sapiens* GN=PRPF38A PE=1 SV=1;

SPF45 HUMAN Splicing factor 45 OS=*Homo sapiens* GN=RBM17 PE=1 SV=1;

SF3A2 HUMAN Splicing factor 3A subunit 2 OS=*Homo sapiens* GN=SF3A2 PE=1 SV=2;

HNRL2 HUMAN Heterogeneous nuclear ribonucleoprotein U-like protein 2OS=*Homo sapiens* GN=HNRNPUL2 PE=1 SV=1;

HNRPC HUMAN Heterogeneous nuclear ribonucleoproteins C1/C2 OS=*Homo sapiens* GN=HNRNPC PE=1 SV=4;

ROA1 HUMAN Heterogeneous nuclear ribonucleoprotein A1 OS=*Homo sapiens* GN=HNRNPA1 PE=1 SV=5;

ROA2 HUMAN Heterogeneous nuclear ribonucleoproteins A2/B1 OS=*Homo sapiens* GN=HNRNPA2B1 PE=1 SV=2;

RAIL2_HUMAN Heterogeneous nuclear ribonucleoprotein A1-like 2 OS=*Homo sapiens* GN=HNRNPA1L2 PE=2 SV=2;

ROA3 HUMAN Heterogeneous nuclear ribonucleoprotein A3 OS=*Homo sapiens* GN=HNRNPA3 PE=1 SV=2;

HNRPM HUMAN Heterogeneous nuclear ribonucleoprotein M OS=*Homo sapiens* GN=HNRNPM PE=1 SV=3;

HNRDL_HUMAN Heterogeneous nuclear ribonucleoprotein D-like OS=*Homo sapiens* GN=HNRNPDL PE=1 SV=3;

ROAO_HUMAN Heterogeneous nuclear ribonucleoprotein A/B OS=*Homo sapiens* GN=HNRNPAB PE=1 SV=2;

ROAA HUMAN Heterogeneous nuclear ribonucleoprotein A/B OS=*Homo sapiens* GN=HNRNPAB PE=1 SV=2;

HNRPK HUMAN Heterogeneous nuclear ribonucleoprotein K OS=*Homo sapiens* GN=HNRNPK PE=1 SV=1;

HNRPL HUMAN Heterogeneous nuclear ribonucleoprotein L OS=*Homo sapiens* GN=HNRNPL PE=1 SV=2;

ROA3_HUMAN Heterogeneous nuclear ribonucleoprotein A3 OS=*Homo sapiens* GN=HNRNPA3 PE=1 SV=2;

ROAO_HUMAN Heterogeneous nuclear ribonucleoprotein AO OS=*Homo sapiens* GN=HNRNPAO PE=1 SV=1; and HNRPU HUMAN Heterogeneous nuclear ribonucleoprotein U OS=*Homo sapiens* GN=HNRNPU PE=1 SV=6.

In yet another aspect, the present invention provides for a composition regulating splicing factors to treat cancer, the composition comprising a PIM kinase inhibitor that exhibits changes and/or disruption of mRNA splicing in combination with a compound that modulates and/or alters activity of an RNA splicing factor.

In a further aspect, the present invention provides for a synergistic combination of therapeutics for treating cancerous tissue and methods for the treatment of human cancers, including daily dosage forms for administration to cancer patients. The present invention provides for synergistic improvements in treatment outcomes by providing for a composition comprising therapeutically synergistic amounts of at least one a PIM kinase inhibitor that exhibits changes of mRNA splicing in combination with a compound that modulates and/or inhibits activity of an RNA splicing factor, such that the combination has a therapeutic effect on cancerous tissue which is greater than the sum of the individual therapeutic effects of the individual compounds.

In another aspect, the present invention provides for a method to identify PIM kinase inhibitors, the method comprising:

contacting a cancer cell comprising at least one RNA splicing factor protein with a compound suspected of having PIM kinase inhibition activity; and determining the changes in splicing of the at least one messenger RNA due to the compound suspected of having PIM kinase inhibition activity relative to a control, wherein such a change would change in splicing of any mRNA would be the biomarker. The method may further comprise determining the level of phosphorylation of the RNA splicing factor after contact with the compound suspected of having PIM kinase inhibition activity.

Further, changes in splicing of such messenger RNAs can be used as biomarkers for patient responsiveness to anti-PIM treatment The PIM kinase inhibitors may include one or more kinases selected from the group consisting of: PIM-1, PIM-2, and PIM-3. Additional PIM kinase modulators/inhibitors, not previously mentioned above, may include but is not limited to 7-chloro-9-ethyl-6-hydroxyisoxazolo[3,4-b]quinoline-3,4(1H,9H)-dione; 2-[[3-(3-chloro-4-fluorophenyl)imidazo[1,2-b]pyridazin-6-yl]amino]butan-1-ol; (Z)-5-(4-propoxybenzylidene)thiazolidine-2,4-dione; (Z)-5-(3-Trifluoromethylbenzylidene)thiazolidine-2,4-dione; N'-(1-(4-Chloro-2-hydroxyphenyl)propylidene)-2-((3-morpholinopropyl)amino-)isonicotinohydrazide; 5-amino-2-(2,6-difluorophenyl)-N-(5-(4-(methylamino)butoxy)isothiazol-4-yl)thiazole-4-carboxamide; 2-(2,6-difluorophenyl)-N-(5-(4-hydroxy-4-methylpentyloxy)isothiazol-4-yl)-5-(methylamino)thiazole-4-carboxamide; (Z)-5-((2-(4-(((6-(furan-2-yl)pyridin-2-yl)methylamino)methyl)piperidin-1-yl)pyrimidin-4-yl)methylene)thiazolidine-2,4-dione; (S)-5-amino-N-(4-(3-aminopiperidin-1-yl)pyridin-3-yl)-2-(2,6-difluorophen-yl)thiazole-4-carboxamide; and N-(4-((3S,5R)-3-amino-5-methylpiperidin-1-yl)pyridin-3-yl)-2-(2,6-difluor-ophenyl)thiazole-4-carboxamide, or a pharmaceutically acceptable salt thereof.

In yet another aspect, the PIM kinase inhibitor is a dual PIM-1/PIM-2 inhibitor. In various cases, the PIM kinase inhibitor is a pan-PIM inhibitor (e.g., inhibitors the activity of each of PIM-1, PIM-2, and PIM-3). One example of a contemplated pan-PIM inhibitor is 5-[[2-[(3R)-3-aminopiperidin-1-yl]biphenyl-3-yl]methylidene]-1,3-thiazoli-dine-2,4-dione (also known as AZD1208).

The cancer to be treated with the proposed combination is one selected from the group consisting of: bone cancer, gynecological cancer, breast cancer, hematological malignancy, skin cancer, liver cancer, kidney cancer, pancreatic cancer, brain cancer, lung cancer, and prostate cancer. The hematological malignancy may be selected from the group consisting of: acute lymphoblastic leukemia (ALL), acute myeloid leukemia (AML), chronic lymphocytic leukemia (CLL), chronic myelogenous leukemia (CML), hairy cell leukemia, AIDS-related lymphoma, B-cell lymphoma, cutaneous T-cell lymphoma, Hodgkin lymphoma, non-Hodgkin lymphoma, mycosis fungoides, primary central nervous system lymphoma, Sezary syndrome, Waldenstrom macroglobulinemia, chronic myeloproliferative disorders, Langerhans cell histiocytosis, multiple myeloma, plasma cell neoplasms, myelodysplastic syndromes, myelodysplastic neoplasms, and myeloproliferative neoplasms.

In one aspect, the hematological malignancy is selected from the group consisting of: B-cell lymphoma and multiple myeloma. For example, the hematological malignancy can be multiple myeloma.

The administration of the PIM kinase inhibitor and a compound that modulates activity of an RNA splicing factor is performed concurrently. Alternatively, the administration of the PIM kinase inhibitor and the compound that modulates and/or inhibits activity of an RNA splicing factor is performed sequentially, wherein the PIM kinase inhibitor is administered before the compound that modulates and/or inhibits activity of an RNA splicing factor or vice versa.

Aspects of the invention described as methods of treatment should also be understood to include first or subsequent "medical use" aspects of the invention or "Swiss use" of compositions for the manufacture of a medicament for treatment of the cancer.

Multiple embodiments are contemplated for combination inventions described herein. For example, some aspects of the invention that are described as a method of treatment (or medical use) combining two or more compounds or agents, preferably in a synergistic amount, whether administered separately (sequentially or simultaneously) or in combination (co-formulated or mixed). For each aspect described in this manner, the invention further includes a composition comprising the two or more compounds or agents co-formulated or in admixture with each other; and the invention further includes a kit or unit dose containing the two or more compounds/agents packaged together. Optionally, such compositions, kits or doses further include one or more carriers with one or both agents or co-packaged for formulation prior to administration to a subject. The reverse also is true: some aspects of the invention are described herein as compositions useful for therapy and containing two or more therapeutic agents. Equivalent methods and uses are specifically contemplated.

Other features and advantages of the disclosure will be apparent from the following detailed description and figures, and from the claims.

BRIEF DESCRIPTION OF THE FIGURES

FIGS. 2 A and B shows validation of splicing factors as in vitro PIM substrates. FIG. 2 A shows a recombinant SRSF1, U2AF1 and BUD13 are direct in-vitro substrates in a PIM Reverse In-Gel Kinase Assay and FIG. 2B show no Pim 2.

FIGS. 4 A and B shows changes in splicing identified after AZD1208 driven inhibition of PIM kinases in MOLM16 (AML) cells, FIG. 4 A shows arrangement of extrons and introns and FIG. 4 B provides numeric changes

FIG. 6** C shows RT-PCR for various splice variants after PIM inhibition in MOLM16 cells (1 µM 6 hrs.). Arrow indicate bands that change after AZD1208 treatment.

DETAILED DESCRIPTION OF THE INVENTION

The present invention provides for a body of knowledge that informs the rational choice of pathways and agents that can be combined with inhibition of the oncogenic PIM family kinases to achieve therapeutic efficacy. Specifically, it has been found that PIM kinase inhibitors disrupt normal mRNA splicing thereby causing altered splice site and/or exon recognition preferences relative to their wild-type counterparts, and can therefore be combined with other agents that alter or influence the mRNA splicing process. As such, it was determined that a suite of proteins that regulate mRNA splicing are direct targets of PIM kinase phosphotransferase activity. Further, changes in splicing of mRNAs can be used as biomarkers for patient responsiveness to anti-PIM treatment and also suggest effective combinatorial therapies, including synergistic, using PIM kinase inhibitors and agents that alter or influence the mRNA splicing process for the treatment of cancers.

PIM kinase inhibitor as provided herein can be any compound that inhibits or modulates the action of a PIM kinase. For example, the compound can inhibit and or modulate one or more of the serine/threonine kinases encoded by a PIM gene or protooncogene. In some embodiments, the serine/threonine kinase is one of three isoforms: PIM-1, PIM-2, and PIM-3. In some aspect, the PIM kinase inhibitors is a pan-PIM inhibitor and inhibits each of PIM-1, PIM-2, and PIM-3. The PIM kinase inhibitor is selective for PIM-1, PIM-2 and/or PIM-3. Examples of PIM kinase inhibitors can be found in: WO 2009/064486 and WO 2012/145617. Further contemplated PIM kinase inhibitors include those found in US20140031360, WO2012/129338, WO2012/148775, WO2013/130660 and WO2014/022752, the disclosures of which are each incorporated by reference herein in their entirety.

As used herein, the term "inhibitor" is meant to describe a compound that blocks, reduces or modulates an activity of an enzyme or system of enzymes, receptors, or other pharmacological target. An inhibitor can act with competitive, uncompetitive, or noncompetitive inhibition. An inhibitor can bind reversibly or irreversibly, and therefore the term includes compounds that are suicide substrates of an enzyme. An inhibitor can modify one or more sites on or near the active site of the enzyme, or it can cause a conformational change elsewhere on the enzyme. The term inhibitor is used more broadly herein than scientific literature so as to also encompass other classes of pharmacologically or therapeutically useful agents, such as agonists, antagonists, stimulants, co-factors, and the like.

A "therapeutically effective amount" of a compound with respect to the subject method of treatment, refers to an amount of the compound(s) in a preparation which, when administered as part of a desired dosage regimen (to a patient, e.g., a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

As used herein, the term "treating" or "treatment" includes reversing, reducing, or arresting one or more symptoms, clinical signs, and underlying pathology of a condition in a manner to improve or stabilize a patient's condition.

As used herein, the term "a synergistic effect" is present when the activity of the active compounds in a combination exceeds the total of the action of the active compounds when applied individually.

Methods of Use

Combination drug therapy is the use of two or more pharmacologic agents administered either separately or in a single dose formulation. The use of combinations can be employed to treat cancer in a patient. For example, the cancer can be a hematological malignancy. In some embodiments, the combinations can be used to increase the efficacy of the individual components, to overcome resistance to a particular agent, or to treat a refractory disease.

Provided herein is a method for treating a cancer in a patient, the method including administering to the patient a therapeutically effective amount of a PIM kinase inhibitor and combine with a compound that modifies and/or inhibits the mRNA splicing process.

As used herein, the term "cancer" includes, but is not limited to, blood borne and solid tumors. Cancer refers to disease of blood, bone, organs, skin tissue, and the vascular system, including, but not limited to, cancers of the bladder, blood, bone, brain, breast, cervix, chest, colon, endometrium, esophagus, eye, head, kidney, liver, lung, lymph nodes, mouth, neck, ovaries, pancreas, prostate, rectum, renal, skin, stomach, testis, throat, and uterus. Specific cancers include, but are not limited to, leukemia (acute lymphocytic leukemia (ALL), acute lyelogenous leukemia (AML), chronic lymphocytic leukemia (CLL), chronic myelogenous leukemia (CML), hairy cell leukemia), mature B cell neoplasms (small lymphocytic lymphoma, B cell prolymphocytic leukemia, lymphoplasmacytic lymphoma (such as Waldenstrom's macroglobulinemia), splenic marginal zone lymphoma, plasma cell myeloma, plasmacytoma, monoclonal immunoglobulin deposition diseases, heavy chain diseases, extranodal marginal zone B cell lymphoma (MALT lymphoma), nodal marginal zone B cell lymphoma (NMZL), follicular lymphoma, mantle cell lymphoma, diffuse B cell lymphoma, diffuse large B cell lymphoma (DLBCL), mediastinal (thymic) large B cell lymphoma, intravascular large B cell lymphoma, primary effusion lymphoma and Burkitt lymphoma/leukemia), mature T cell and natural killer (NK) cell neoplasms (T cell prolymphocytic leukemia, T cell large granular lymphocytic leukemia, aggressive NK cell leukemia, adult T cell leukemia/lymphoma, extranodal NK/T cell lymphoma, enteropathy-type T cell lymphoma, hepatosplenic T cell lymphoma, blastic NK cell lymphoma, mycosis fungoides (Sezary syndrome), primary cutaneous anaplastic large cell lymphoma, lymphomatoid papulosis, angioimmunoblastic T cell lymphoma, unspecified peripheral T cell lymphoma and anaplastic large cell lymphoma), Hodgkin lymphoma (nodular sclerosis, mixed celluarity, lymphocyte-rich, lymphocyte depleted or not depleted, nodular lymphocyte-predominant), myeloma (multiple myeloma, indolent myeloma, smoldering myeloma), chronic myeloproliferative disease, myelodysplastic/myeloproliferative disease, myelodysplastic syndromes, immunodeficiency-associated lymphoproliferative disorders, histiocytic and dendritic cell neoplasms, mastocytosis, chondrosarcoma, Ewing sarcoma, fibrosarcoma, malignant giant cell tumor, myeloma bone disease, osteosarcoma, breast cancer (hormone dependent, hormone independent), gynecological cancers (cervical, endometrial, fallopian tube, gestational trophoblastic disease, ovarian, peritoneal, uterine, vaginal and vulvar), basal cell carcinoma (BCC), squamous cell carcinoma (SCC), malignant melanoma, dermatofibrosarcoma protuberans, Merkel cell carcinoma, Kaposi's sarcoma, astrocytoma, pilocytic astrocytoma, dysembryoplastic neuroepithelial tumor, oligodendrogliomas, ependymoma, glioblastoma multiforme, mixed gliomas, oligoastrocytomas, medulloblastoma, retinoblastoma, neuroblastoma, germinoma, teratoma, malignant mesothelioma (peritoneal mesothelioma, pericardial mesothelioma, pleural mesothelioma), gastro-entero-pancreatic or gastroenteropancreatic neuroendocrine tumor (GEP-NET), carcinoid, pancreatic endocrine tumor (PET), pancreatic adenocarcinoma, colorectal adenocarcinoma, colorectal carcinoma, aggressive neuroendocrine tumor, leiomyosarcomamucinous adenocarcinoma, Signet Ring cell adenocarcinoma, hepatocellular carcinoma, cholangiocarcinoma, hepatoblastoma, hemangioma, hepatic adenoma, focal nodular hyperplasia (nodular regenerative hyperplasia, hamartoma), non-small cell lung carcinoma (NSCLC) (squamous cell lung carcinoma, adenocarcinoma, large cell lung carcinoma), small cell lung carcinoma, lung cancer, thyroid carcinoma, prostate cancer (hormone refractory, androgen independent, androgen dependent, hormone-insensitive), and soft tissue sarcomas (fibrosarcoma, malignant fibrous hystiocytoma, dermatofibrosarcoma, liposarcoma, rhabdomyosarcoma leiomyosarcoma, hemangiosarcoma, synovial sarcoma, malignant peripheral nerve sheath tumor/neurofibrosarcoma, extraskeletal osteosarcoma).

Many tumors of the hematopoietic and lymphoid tissues are characterized by an increase in cell proliferation, or a particular type of cell. The chronic myeloproliferative diseases (CMPDs) are clonal hematopoietic stem cell disorders characterized by proliferation in the bone marrow of one or more of the myeloid lineages, resulting in increased numbers of granulocytes, red blood cells and/or platelets in the peripheral blood. CMPD can include chronic myelogenous leukemia, chronic neutrophilic leukemia, chronic eosinophilic leukemia, polycythaemia vera, chronic idiopathic myelofibrosis, essential thrombocythaemia and unclassifiable chronic myeloproliferative disease.

Provided herein is a method for treating a hematological malignancy in a patient, the method including administering to the patient a therapeutically effective amount of a PIM kinase inhibitor and in combination with a compound that modifies and/or inhibits the mRNA splicing process.

The term "hematological malignancy" as used herein is meant to include cancers that affect one or more of the blood, bone marrow, and lymph nodes, such as acute lymphoblastic leukemia (ALL), acute myeloid leukemia (AML), chronic lymphocytic leukemia (CLL), chronic myelogenous leukemia (CML), hairy cell leukemia, AIDS-related lymphoma, B-cell lymphoma, cutaneous T-cell lymphoma, Hodgkin lymphoma, non-Hodgkin lymphoma, mycosis fungoides, primary central nervous system lymphoma, Sezary syndrome, Waldenstrom macroglobulinemia, chronic myeloproliferative disorders, Langerhans cell histiocytosis, multiple myeloma, plasma cell neoplasms, myelodysplastic syndromes, myelodysplastic neoplasms, and myeloproliferative neoplasms.

A "patient" as used herein refers to a mammal. For example, the mammal may be a mouse, rat, guinea pig, dog, monkey, or chimpanzee. Another example of a mammal is a human.

Administration

Compositions prepared as described herein can be administered in various forms, depending on the disorder to be treated and the age, condition, and body weight of the patient, as is well known in the art. For example, where the compositions are to be administered orally, they may be formulated as tablets, capsules, granules, powders, or syrups; or for parenteral administration, they may be formulated as injections (intravenous, intramuscular, or subcutaneous), drop infusion preparations, or suppositories.

Although the dosage will vary depending on the symptoms, age and body weight of the patient, the nature and severity of the disorder to be treated or prevented, the route of administration and the form of the drug, in general, a daily dosage of from 0.001 to 2000 mg of the different compounds is recommended for an adult human patient, and this may be administered in a single dose or in divided doses.

The phrase "pharmaceutically acceptable" is employed herein to refer to those ligands, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

In solid dosage forms for oral administration (capsules, tablets, pills, powders, granules, and the like), the active ingredients are mixed with one or more pharmaceutically acceptable carriers, such as sodium citrate or dicalcium phosphate, and/or any of the following: (1) fillers or extenders, such as starches, cyclodextrins, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. Solid compositions of a similar type may also be employed as fillers in soft and hard-filled gelatin capsules using such excipients as lactose or milk sugars, as well as high molecular weight polyethylene glycols, and the like.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents, and emulsifiers such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols, and fatty acid esters of sorbitan, and mixtures thereof.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection, and infusion.

The precise time of administration and/or amount of the composition that will yield the most effective results in terms of efficacy of treatment in a given patient will depend upon the activity, pharmacokinetics, and bioavailability of a particular compound, physiological condition of the patient (including age, sex, disease type and stage, general physical condition, responsiveness to a given dosage, and type of medication), route of administration, etc. However, the above guidelines can be used as the basis for fine-tuning the treatment, e.g., determining the optimum time and/or amount of administration, which will require no more than routine experimentation consisting of monitoring the patient and adjusting the dosage and/or timing.

The concentration of a disclosed compounds in a pharmaceutically acceptable mixture will vary depending on several factors, including the dosage of the compound to be administered, the pharmacokinetic characteristics of the compound(s) employed, and the route of administration. In general, the compositions provided herein may be provided in an aqueous solution containing about 0.1-10% w/v of a compound disclosed herein, among other substances, for parenteral administration. Typical dose ranges are from about 0.01 to about 50 mg/kg of body weight per day, given in 1-4 divided doses. Each divided dose may contain the same or different compounds. The dosage will be an effective amount depending on several factors including the overall health of a patient, and the formulation and route of administration of the selected compound(s).

In some embodiments, the weight ratio of a PIM kinase inhibitor to a compound that modulates and/or inhibits activity of an RNA splicing factor protein providing for the synergistic effect on cancer cells lies within the range from about 20:0.001 to 0.01:20, alternatively from about 15:0.01 to 1:0.0005, and alternatively from 12:1 to 1:0.0005. Other specific and preferred ratios are given in the examples.

Examples

Reverse in-Gel Kinase Assay (RIKA)

Figure 1:
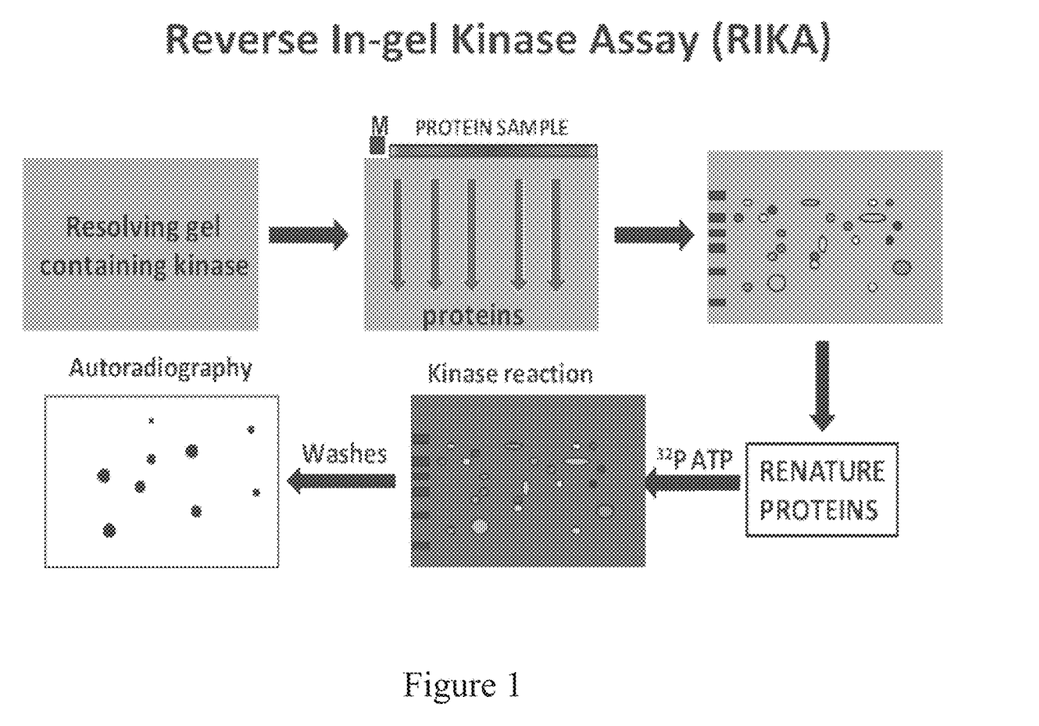
FIG. 1 is a schematic representation of 2D Reverse in gel kinase assay (RIKA).

The present invention shows that PIM kinase inhibitors disrupt and/or changes normal mRNA splicing and can therefore be combined with other agents that modify and/or inhibit mRNA splicing. This was achieved by profiling PIM kinase substrates using a reverse in-gel kinase assay (RIKA) as described in U.S. Pat. No. 7,368,258, the contents included herein for all purposes, and determining that a suite of proteins that regulate mRNA splicing are direct targets of PIM kinase phosphotransferase activity. FIG. 1 shows a schematic representation of 2D RIKA. Briefly, the kinase is polymerized in a denaturing gel. The proteins are separated by two dimensional gel electrophoresis. The kinase and separated proteins are refolded in the gel using a de-escalating chaotropic agent gradient, for example, using decreasing molarities of urea. The kinase and separated proteins are incubated in isotopically labeled ATP, for example, $\gamma^{32}$P-ATP or $^{18}$O-ATP. This step labels the substrates for the kinase. Excess ATP is washed away by multiple washes and gels are visualized by autoradiography, or $^{18}$O-labeled peptides are extracted from the gel and identified using mass spectrometry.

The list of splicing-related direct PIM kinase targets is shown below in Table 1:

TABLE 1

| Serial Number | Entry Name | Protein Name |
|---|---|---|
| 1 | SRSF1_HUMAN | Serine/arginine-rich splicing factor 1 OS = Homo sapiens GN = SRSF1 PE = 1 SV = 2 |
| 2 | SRSF5_HUMAN | Serine/arginine-rich splicing factor 5 OS = Homo sapiens GN = SRSF5 PE = 1 SV = 1 |
| 3 | SRSF6_HUMAN | Serine/arginine-rich splicing factor 6 OS = Homo sapiens GN = SRSF6 PE = 1 SV = 2 |
| 4 | SRSF7_HUMAN | Serine/arginine-rich splicing factor 7 OS = Homo sapiens GN = SRSF7 PE = 1 SV = 1 |
| 5 | SRS10_HUMAN | Serine/arginine-rich splicing factor 10 OS = Homo sapiens GN = SRSF10 PE = 1 SV = 1 |
| 6 | U2AF1_HUMAN | Splicing factor U2AF 35 kDa subunit OS = Homo sapiens GN = U2AF1 PE = 1 SV = 3 |
| 7 | CWC22_HUMAN | Pre-mRNA-splicing factor CWC22 homolog OS = Homo sapiens GN = CWC22 PE = 1 SV = 3 |
| 8 | SF3B2_HUMAN | Splicing factor 3B subunit 2 OS = Homo sapiens GN = SF3B2 PE = 1 SV = 2 |
| 9 | SF01_HUMAN | Splicing factor 1 OS = Homo sapiens GN = SF1 PE = 1 SV = 4 |
| 10 | SFR19_HUMAN | Splicing factor, arginine/serine-rich 19 OS = Homo sapiens GN = SCAF1 PE = 1 SV = 3 |
| 11 | PR38A_HUMAN | Pre-mRNA-splicing factor 38A OS = Homo sapiens GN = PRPF38A PE = 1 SV = 1 |
| 12 | SPF45_HUMAN | Splicing factor 45 OS = Homo sapiens GN = RBM17 PE = 1 SV = 1 |
| 13 | SF3A2_HUMAN | Splicing factor 3A subunit 2 OS = Homo sapiens GN = SF3A2 PE = 1 SV = 2 |
| 14 | HNRL2_HUMAN | Heterogeneous nuclear ribonucleoprotein U-like protein 2 OS = Homo sapiens GN = HNRNPUL2 PE = 1 SV = 1 |
| 15 | HNRPC_HUMAN | Heterogeneous nuclear ribonucleoproteins C1/C2 OS = Homo sapiens GN = HNRNPC PE = 1 SV = 4 |
| 16 | ROA1_HUMAN | Heterogeneous nuclear ribonucleoprotein A1 OS = Homo sapiens GN = HNRNPA1 PE = 1 SV = 5 |
| 17 | ROA2_HUMAN | Heterogeneous nuclear ribonucleoproteins A2/B1 OS = Homo sapiens GN = HNRNPA2B1 PE = 1 SV = 2 |
| 18 | RA1L2_HUMAN | Heterogeneous nuclear ribonucleoprotein A1-like 2 OS = Homo sapiens GN = HNRNPA1L2 PE = 2 SV = 2 |
| 19 | ROA3_HUMAN | Heterogeneous nuclear ribonucleoprotein A3 OS = Homo sapiens GN = HNRNPA3 PE = 1 SV = 2 |
| 20 | HNRPM_HUMAN | Heterogeneous nuclear ribonucleoprotein M OS = Homo sapiens GN = HNRNPM PE = 1 SV = 3 |
| 21 | HNRDL_HUMAN | Heterogeneous nuclear ribonucleoprotein D-like OS = Homo sapiens GN = HNRNPDL PE = 1 SV = 3 |
| 22 | ROAA_HUMAN | Heterogeneous nuclear ribonucleoprotein A/B OS = Homo sapiens GN = HNRNPAB PE = 1 SV = 2 |
| 23 | ROAA_HUMAN | Heterogeneous nuclear ribonucleoprotein A/B OS = Homo sapiens GN = HNRNPAB PE = 1 SV = 2 |
| 24 | HNRPK_HUMAN | Heterogeneous nuclear ribonucleoprotein K OS = Homo sapiens GN = HNRNPK PE = 1 SV = 1 |
| 25 | HNRPL_HUMAN | Heterogeneous nuclear ribonucleoprotein L OS = Homo sapiens GN = HNRNPL PE = 1 SV = 2 |
| 26 | ROA3_HUMAN | Heterogeneous nuclear ribonucleoprotein A3 OS = Homo sapiens GN = HNRNPA3 PE = 1 SV = 2 |
| 27 | ROA0_HUMAN | Heterogeneous nuclear ribonucleoprotein A0 OS = Homo sapiens GN = HNRNPA0 PE = 1 SV = 1 |
| 28 | HNRPU_HUMAN | Heterogeneous nuclear ribonucleoprotein U OS = Homo sapiens GN = HNRNPU PE = 1 SV = 6 |

Confirmation of Proteins as PIM Substrates

Figure 2:
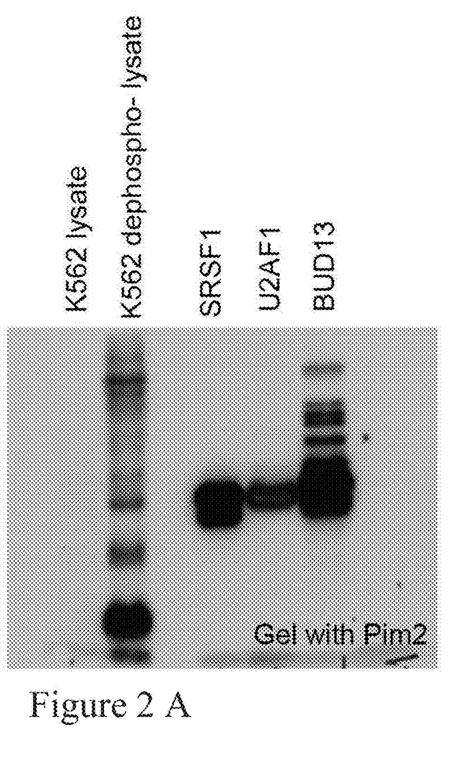

To validate a subset of the proteins set forth in Table 1 as PIM substrates, recombinant proteins were produced in *E. coli* cells and then a PIM 2 RIKA was performed in presence of $\gamma^{32}$P-ATP. Once the protein is phosphorylated by PIM 2 in the gel, in presence of $\gamma^{32}$P-ATP, the protein is labeled with radioactive phosphate. The phosphorylation can then be visualized by exposing the SDS-PAGE gel against an X-ray film. Upon auto-radiographic visualization it was confirmed that SRSF1, U2AF1 and BUD13 proteins were validated as PIM 2 substrates. The gel containing PIM2 on the left shows signal due to phosphorylation of these substrates in RIKA, however, the control gel without kinase does not show any signal, as shown in FIG. 2.

Figure 3:
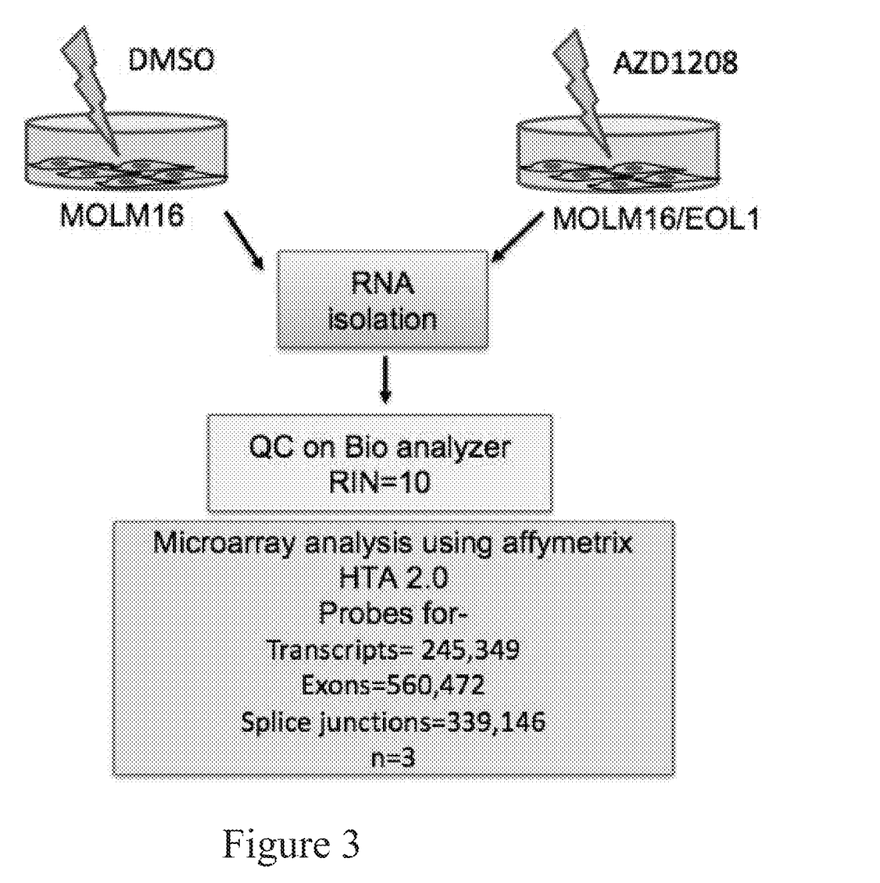
FIG. 3 shows a schematic representation of procedure for microarray analysis.
Figure 4:
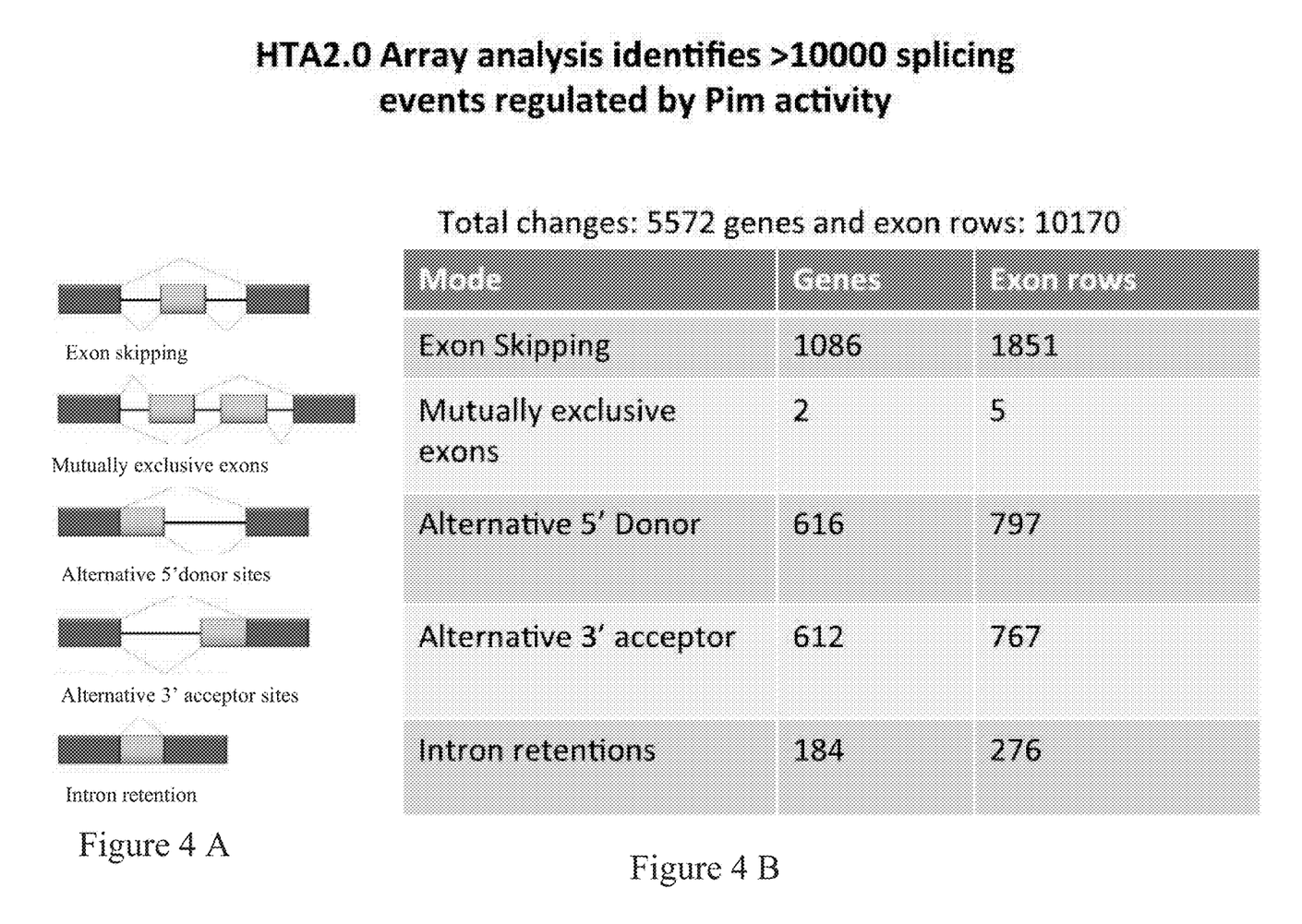
Figure 5:
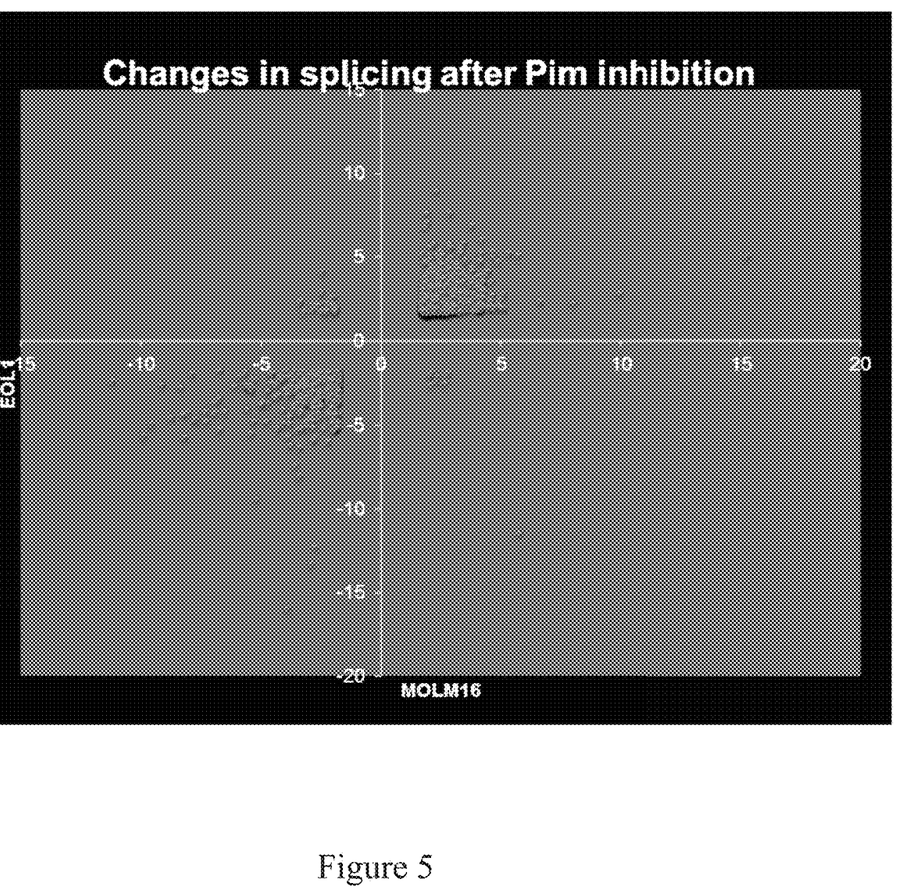
FIG. 5 shows changes in splicing after PIM inhibition.

Identification of Novel Splicing Changes by PIM Kinase Inhibition in MOLM16 and EOL1 Cells:

Due to the large number of splicing factors as PIM substrates, a more globally spread regulation of splicing by PIM kinases was envisioned. As such, a microarray approach was chosen to profile the entire transcriptome for changes in alternative splicing, due to inhibition of PIM kinase activity. MOLM16 cells were treated with DMSO/AZD1208 (1 µM) (pan-PIM inhibitor) for 6 hours. This experiment was performed in triplicates and RNA was run on a bioanalyzer to confirm sample intergrity, as outline in FIG. 3. A similar procedure was used for analysis of both MOLM16 and EOL1 cells. After 1 µM AZD1208 treatment for 6 hours, cells were harvested, and total RNA was isolated. The RNA quality was confirmed using a bio-analyzer. High quality RNA samples were further processed and hybridized to Affymetrix HTA 2.0 microarrays. The results obtained were processed using Affymetrix expression console and transcriptome analysis console (TAC) software. The microarray results as shown in FIG. 4, as expected, showed wide spread changes in splicing indices in >10,000 splicing events in >5000 gene products. Similar experiment was also performed for EOL1 cells. In EOL1 cells as well, widespread changes were observed in splicing after PIM kinase inhibition by AZD1208 (1 µM, 6 hrs.). FIG. 5 shows changes in splicing after PIM kinase inhibition for the two cell lines. Each point represents a unique probe selection region and the splicing index values for MOLM16 (X axis) and EOL1 cells (Y axis) are shown. All the points in +X+Y and −X−Y quadrants are splicing changes consistent with directionality of the change. The few changes in quadrant −X+Y and +X−Y showed the opposite direction of change. Microsoft Excel functions were used to identify the overlap between these lists of splicing changes. When these lists were compared, 2599 changes were observed in similar probe selection regions. When the directionality of these changes was considered, it was noted that most of these changes were also consistantly in the same direction (all but 39 out of 2599). This suggest that the effect on exon inclusion or exon exclusion was similar between these cell lines.

Validation of Microarray Targets

Figure 6A:
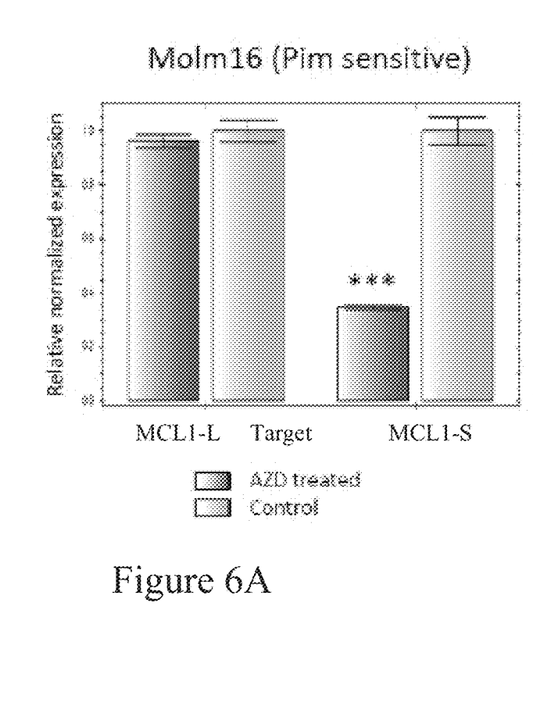
FIG. 6A shows qRT-PCR for MCL1 splice variants after PIM inhibition in MOLM16 and FIG. 6B shows OCI-MI cells treated with AZD1208 (1 µM) 6 hrs. * p<0.001. Control=DMSO treated.
Figure 6B:
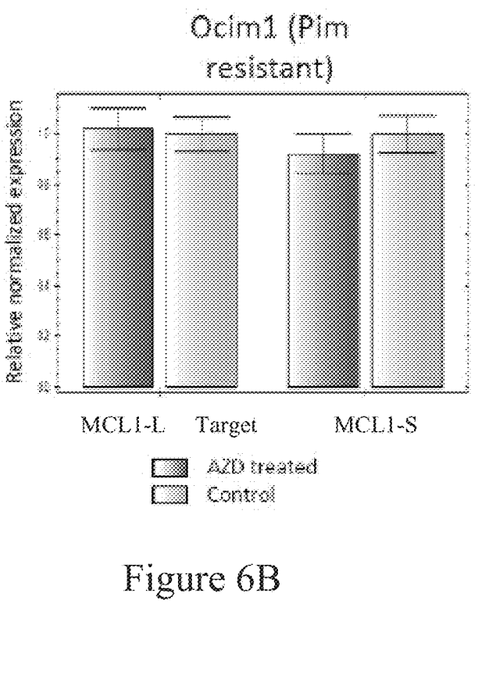
Figure 6C:
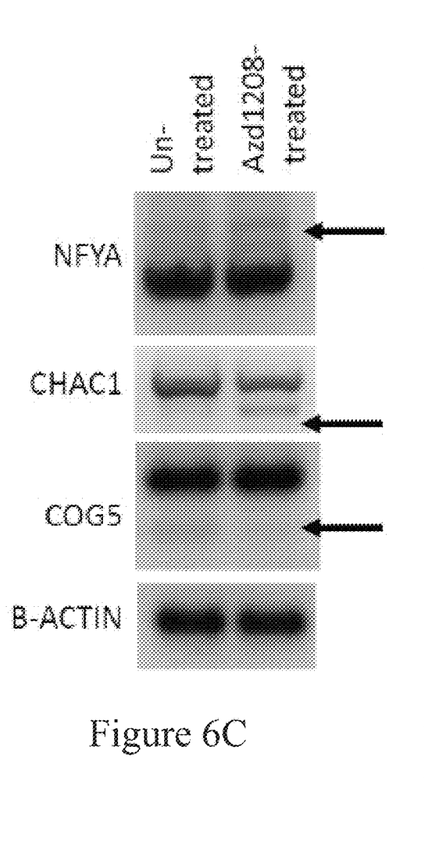

A few targets from the microarray data were chosen, that being, ones that were affected by PIM kinase inhibition. The procedure was manual curation of data, followed by reference seq analysis of splice variants to determine avalibilty of sequence information. Initially, changes in splice variants of a known apoptotic regulator, MCL1 were validated. The smaller isoform of MCL1 is pro-apotic, while the longer isoform has anti-apotic functions. After PIM inhibition, the shorter isoform of MCl1 specifically and significantly reduces as seen by Taqman assay based qRT-PCR and shown in FIG. 6A. This regulation was only observed in PIM-sensitive MOLM16 cells, AZD1208 resistant OCI-M1 cells did not show any change in level of both the splice variants. Three other targets, CHAC1, NFYA and Cog5 by RT-PCR were also validated in MOLM16 cells as shown in FIG. 6B. The changes were in agreement with the microarray data.

Phosphorylation of Splicing Factors

Figure 7:
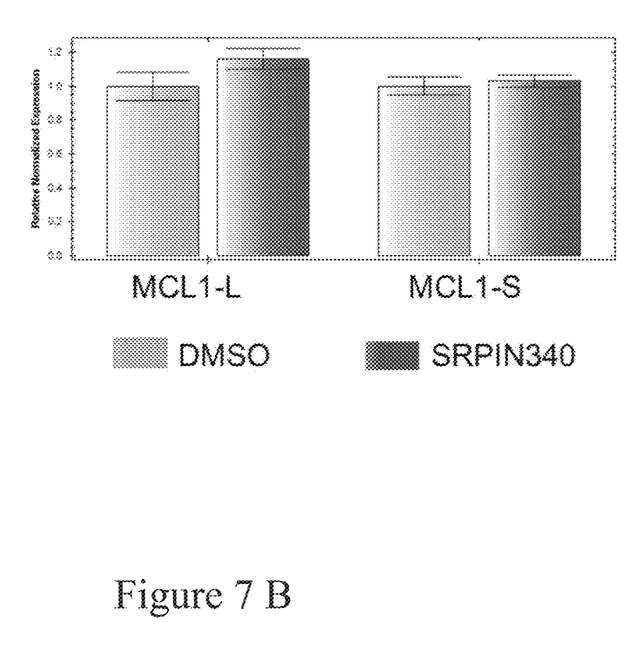
FIG. 7A shows western blot analysis using phospho-SR antibody. MOLM16 and EOL1 cells were treated with AZD1208 or SRPIN340 for indicated concentration and time. Cells lysates from treated cells were used for western blot analysis. SRPIN treated samples show reduction in phosphorylation signal compared to DMSO treated controls, but not AZD1208 treated samples.
FIG. 7B shows qRT-PCR for MCL1 splice variants after PIM inhibition in MOLM16 with SRPIN340 (20 µM 24 hours).

Phosphorylation of splicing factors is known to play a role in regulation of splicing. Phosphorylation of splicing factors called serine arginine rich proteins (SR proteins) is known to regulate their function and localization. Serine arginine rich protein kinases (SRPK1 and SRPK2) phosphorylate these proteins and inhibition of SRPK activity using the small molecule modulator SRPIN340 leads to reduction in phosphorylation. The level of SR protein phosphorylation can be visualized using phospho-SR protein antibody. It was investigated to determine if PIM kinases regulate SRPK activity to indirectly lead to changes in splicing. Western blot of MOLM16 and EOL1 cells using phospho-SR protein antibody shows that although phosphorylation of SR proteins changes after SRPIN340 treatment, treatment with PIM inhibitor AZD1208 does not change SR protein phosphorylation, as shown in FIG. 7A. Thus, it was concluded that the SRPK activity was not affected by PIM kinase inhibition. That also suggests that the splicing changes observed by PIM kinase inhibition are independent and not caused by indirect SRPK inhibition. To further validate this result, it was investigated if inhibition of SRPK activity by SRPIN340 caused changes in MCL1 splicing. Changes in MCL1 splicing were not observed after 24-hour treatment with 20 µM SRPIN340 treatment. This result shown in FIG. 7B validates that this change in splicing is independent of SRPK activity.

Combination of PIM Kinase Inhibitor (AZD1208) Synergizes with RNA Splicing Modulator/Inhibitor (SRPIN340 or Pladienolide B)

General experimental procedure: 10,000 (MOLM16) or 20,000 (EOL1) cells were seeded per well in 96-well plates. After culturing overnight, AZD1208 and/or Pladienolide B/SRPIN340 were added to wells in quadruplicates at 5 different concentrations. Different ratios between AZD1208 and Pladienolide B were tried in MOLM16 and EOL1 cells. At 48 hours the MTT metabolism indicative of number of live cells was measured by MTT assay (Promega, Cat: G4000). The resulting values were used to evaluate the Fa (fraction affected) values, which were plugged into the Compusyn software to calculate the combination indices (CI values) at ED50, ED75, ED90 and ED95 (ED—Effective dose of combination).

MOLM16 cells: Experiment Trial 1: Combination tested—AZD1208: Pladienolide B (ratio 0.12:0.01)

| Azd1208 (µM) | Effect | Pladienolide B (µM) | Effect | Combination (µM) | Effect |
|---|---|---|---|---|---|
| 0.12 | 0.614 | 0.01 | 0.757 | 0.12 + 0.01 | 0.859 |
| 0.096 | 0.594 | 0.008 | 0.726 | 0.096 + 0.008 | 0.827 |
| 0.072 | 0.564 | 0.006 | 0.711 | 0.072 + 0.006 | 0.837 |
| 0.048 | 0.471 | 0.004 | 0.599 | 0.048 + 0.004 | 0.764 |
| 0.024 | 0.415 | 0.002 | 0.517 | 0.024 + 0.002 | 0.69 |

These values of drug dose and effect (fraction of cells affected by the treatment—FA values) were input into the Compusyn software to estimate the interaction between the two drugs.

Compusyn Results: CI Values

| Combination | ED50 | ED75 | ED90 | ED95 |
|---|---|---|---|---|
| Azd + PladB | 0.42366 | 0.44572 | 0.48713 | 0.52629 |

Combination indices (CI values) represent the interaction between the drugs—CI>1 shows antagonism, CI=1 shows additive effect, CI<1 shows synergy. A lower CI value shows the stronger synergy. AZD1208 and Pladienolide B show strong synergy and also shows that a small amount of Pladienolide B can reduce the amount of AZD1208 required to achieve the same effect.

MOLM16 cells: Experiment Trial 2: Combination tested—AZD1208: Pladienolide B (ratio 0.12:0.01)

| Azd1208 (µM) | Effect | Pladienolide B (µM) | Effect | Combination (µM) | Effect |
|---|---|---|---|---|---|
| 0.12 | 0.622 | 0.01 | 0.862 | 0.12 + 0.01 | 0.923 |
| 0.096 | 0.566 | 0.008 | 0.821 | 0.096 + 0.008 | 0.905 |
| 0.072 | 0.534 | 0.006 | 0.752 | 0.072 + 0.006 | 0.875 |
| 0.048 | 0.478 | 0.004 | 0.676 | 0.048 + 0.004 | 0.846 |
| 0.024 | 0.337 | 0.002 | 0.487 | 0.024 + 0.002 | 0.689 |

Compusyn Results: CI Values

| Combination | ED50 | ED75 | ED90 | ED95 |
|---|---|---|---|---|
| Azd + PladB | 0.57625 | 0.56166 | 0.58012 | 0.60660 |

Combination indices (CI values) represent the interaction between the drugs—CI>1 shows antagonism, CI=1 shows additive effect, CI<1 shows synergy. A lower CI value shows the stronger synergy. In this trial as well, AZD1208 and Pladienolide B show strong synergy.

MOLM16 cells: Experiment Trial 3: Combination tested—AZD1208: Pladienolide B (ratio 0.12:0.01)

| Azd1208 (μM) | Effect | Pladienolide B (μM) | Effect | Combination (μM) | Effect |
|---|---|---|---|---|---|
| 0.12 | 0.606 | 0.01 | 0.814 | 0.12 + 0.01 | 0.906 |
| 0.096 | 0.554 | 0.008 | 0.749 | 0.096 + 0.008 | 0.876 |
| 0.072 | 0.524 | 0.006 | 0.696 | 0.072 + 0.006 | 0.862 |
| 0.048 | 0.455 | 0.004 | 0.607 | 0.048 + 0.004 | 0.820 |
| 0.024 | 0.344 | 0.002 | 0.393 | 0.024 + 0.002 | 0.650 |

Compusyn Results: CI Values

| Combination | ED50 | ED75 | ED90 | ED95 |
|---|---|---|---|---|
| Azd + PladB | 0.52227 | 0.50387 | 0.52998 | 0.56641 |

Combination indices (CI values) represent the interaction between the drugs—CI>1 shows antagonism, CI=1 shows additive effect, CI<1 shows synergy. A lower CI value shows the stronger synergy. In the third trial as well, AZD1208 and Pladienolide B show strong synergy.

Figure 8:
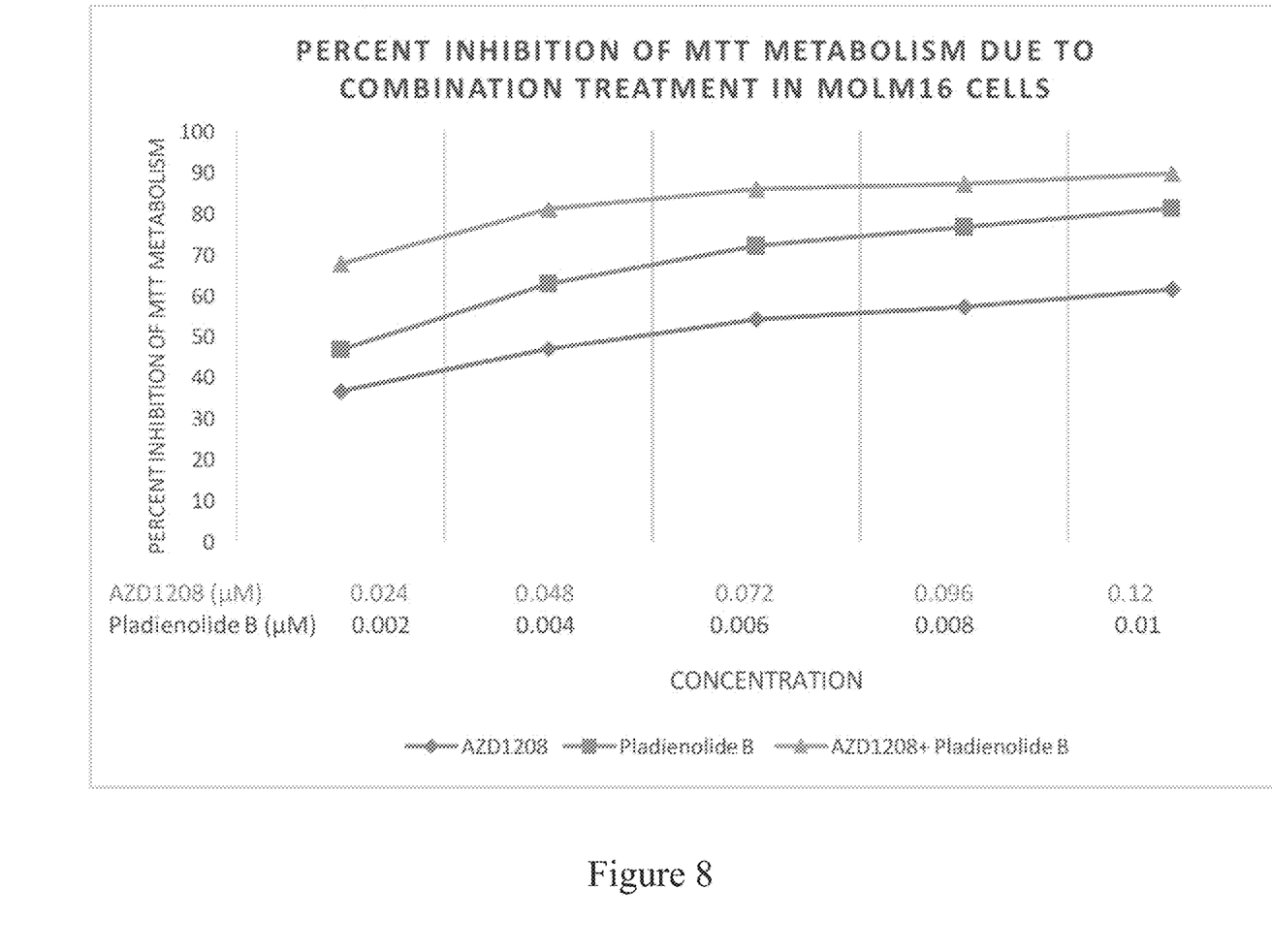
FIG. 8 shows the results of average MTT inhibition for three independent experiments after treatment with single inhibitors and combination.

FIG. 8 shows the results of average MTT inhibition for three above-discussed independent experiments after treatment with single inhibitors and then the combination. Clearly the combination is always more effective in comparison to individual treatments and the results of the Compusyn calculation show a synergistic effect.

Testing with SRPIN340. A Small Molecule Modulator of SRPK1 (Serine-Arginine Protein Kinase 1)

MOLM16 cells: Experiment Trial 1: Combination tested—AZD1208: SRPIN340 (ratio 0.12:20)

| Azd1208 (μM) | Effect | SRPIN340 (μM) | Effect | Combination (μM) | Effect |
|---|---|---|---|---|---|
| 0.12 | 0.628 | 20 | 0.385 | 0.12 + 20 | 0.779 |
| 0.06 | 0.521 | 10 | 0.014 | 0.06 + 10 | 0.685 |
| 0.03 | 0.396 | 5 | 0.004 | 0.03 + 5 | 0.636 |

These values of drug dose and effect (fraction of cells affected by the treatment—FA values) were input into the Compusyn software to estimate the interaction between the two drugs.

Compusyn Results: CI values

| Combination | ED50 | ED75 | ED90 | ED95 |
|---|---|---|---|---|
| Azd + SRPIN | 0.24541 | 0.58223 | 1.78144 | 4.39339 |

Combination indices (CI values) represent the interaction between the drugs—CI>1 shows antagonism, CI=1 shows additive effect, CI<1 shows synergy. A lower CI value shows the stronger synergy. Although higher ED values show antagonism between the two drugs, these drugs show very strong synergy at lower effective dose of combination.

Testing in EOL Cells

To further confirm the finding in MOLM16 cells, it was tested whether the combination of AZD1208 and Pladienolide B is synergistic in another AML cell line—EOL1. Different ratios between AZD1208 and Pladienolide B were tested to identify the ideal ratio that provides maximum synergy.

EOL1 cells: Experiment Trial 1: Combination tested—AZD1208: Pladienolide B (ratio 0.12:0.005)

| Azd1208 (μM) | Effect | Pladienolide B (μM) | Effect | Combination (μM) | Effect |
|---|---|---|---|---|---|
| 0.12 | 0.680 | 0.005 | 0.982 | 0.12 + 0.005 | 0.990 |
| 0.096 | 0.684 | 0.004 | 0.957 | 0.096 + 0.004 | 0.988 |
| 0.072 | 0.675 | 0.003 | 0.890 | 0.072 + 0.003 | 0.974 |
| 0.048 | 0.529 | 0.002 | 0.633 | 0.048 + 0.002 | 0.883 |
| 0.024 | 0.395 | 0.001 | 0.315 | 0.024 + 0.001 | 0.619 |

Compusyn Results: CI Values

| Combination | ED50 | ED75 | ED90 | ED95 |
|---|---|---|---|---|
| Azd + PladB | 1.12957 | 0.81959 | 0.71821 | 0.69802 |

Combination indices (CI values) represent the interaction between the drugs—CI>1 shows antagonism, CI=1 shows additive effect, CI<1 shows synergy. A lower CI value shows the stronger synergy. The combination shows synergy at higher effective dose (ED), however at lower ED values the combination is antagonistic.

Since the cells were more sensitive to Pladienolide B than AZD1208, a lower concentration of Pladienolide B was used in the next experiment to compare the effect of both the drugs equally.

2). EOL1 cells: Experiment Trial 2: Combination tested—AZD1208: Pladienolide B (Ratio 0.12:0.0025)

| Azd1208 (μM) | Effect | Pladienolide B (μM) | Effect | Combination (μM) | Effect |
|---|---|---|---|---|---|
| 0.12 | 0.698 | 0.0025 | 0.820 | 0.12 + 0.0025 | 0.965 |
| 0.096 | 0.683 | 0.002 | 0.706 | 0.096 + 0.002 | 0.962 |
| 0.072 | 0.650 | 0.0015 | 0.528 | 0.072 + 0.0015 | 0.895 |
| 0.048 | 0.587 | 0.001 | 0.351 | 0.048 + 0.001 | 0.766 |
| 0.024 | 0.432 | 0.0005 | 0.060 | 0.024 + 0.0005 | 0.495 |

These values of drug dose and effect (fraction of cells affected by the treatment—FA values) were input into the Compusyn software to estimate the interaction between the two drugs.

Compusyn Results: CI Values

| Combination | ED50 | ED75 | ED90 | ED95 |
|---|---|---|---|---|
| Azd + PladB | 1.16996 | 0.68199 | 0.53605 | 0.51099 |

Combination indices (CI values) represent the interaction between the drugs—CI>1 shows antagonism, CI=1 shows additive effect, CI<1 shows synergy. A lower CI value shows the stronger synergy. AZD1208 and Pladienolide B show strong synergy at the higher effective doses (ED), and at ED50 the combination is weakly antagonistic.

3) EOL1 Cells: Experiment Trial 3: Combination Tested—AZD1208: Pladienolide B (Ratio 0.12:0.0025)

| Azd1208 (μM) | Effect | Pladienolide B (μM) | Effect | Combination (μM) | Effect |
|---|---|---|---|---|---|
| 0.12 | 0.642 | 0.0025 | 0.814 | 0.12 + 0.0025 | 0.964 |
| 0.096 | 0.633 | 0.002 | 0.667 | 0.096 + 0.002 | 0.927 |
| 0.072 | 0.600 | 0.0015 | 0.542 | 0.072 + 0.0015 | 0.853 |
| 0.048 | 0.523 | 0.001 | 0.360 | 0.048 + 0.001 | 0.732 |
| 0.024 | 0.373 | 0.0005 | 0.095 | 0.024 + 0.0005 | 0.442 |

These values of drug dose and effect (fraction of cells affected by the treatment—FA values) were input into the Compusyn software to estimate the interaction between the two drugs.

Compusyn Results: CI Values

| Combination | ED50 | ED75 | ED90 | ED95 |
|---|---|---|---|---|
| Azd + PladB | 1.05950 | 0.66767 | 0.53497 | 0.50218 |

Combination indices (CI values) represent the interaction between the drugs—CI>1 shows antagonism, CI=1 shows additive effect, CI<1 shows synergy. A lower CI value shows the stronger synergy. AZD1208 and Pladienolide B show strong synergy at the higher effective doses (ED), and at ED50 the combination is additive, since the value is very close to 1.

The invention claimed is:

1. A composition comprising a combination of therapeutically synergistic amounts of at least one a PIM kinase inhibitor that exhibits changes and/or disruption of mRNA splicing in combination with a compound that modulates and/or inhibits splicing activity of an RNA splicing factor for the treatment of cancer, wherein the at least one PIM kinase inhibitor is SGI-1776 (N-[(1-methylpiperidin-4-yl) methyl]-3-[3-(trifluoromethoxy)phenyl]imidazo[1,2-b] pyridazin-6-amine), SMI-4a (5-[[3-(trifluoromethyl)phenyl] methylidene]-1,3-thiazolidine-2,4-dione), CX-6258 (E)-5-chloro-3-((5-(3-(4-methyl-1,4-diazepane-1-carbonyl) phenyl)furan-2-yl)methylene)indolin-2-one), LKB1 (N-[5-(4-cyanophenyl)-1H-pyrrolo[2,3-b]pyridin-3-yl]pyridine-3-carboxamide), AZD1208 ((5E)-5-[[2-[(3R)-3-aminopiperidin-1-yl]-3-phenylphenyl]methylidene]-1,3-thiazolidine-2,4-dione), PIM-1 Inhibitor 2 (4-[3-(4-chlorophenyl)-2,1-benzoxazol-5-yl]pyrimidin-2-amine), R8-T198 wt and TCS PIM-1 (6-(5-bromo-2-hydroxyphenyl)-2-oxo-4-phenyl-1,2-dihydropyridine-3-carbonitrile), and wherein the compound that modulates and/or inhibits splicing activity of a RNA splicing factor is natural product of *Pseudomonas* sp. number 2663 (FR901464), natural products from *Streptomyces platensis* Mer-11107, pladienolide B, herboxidien, trichostatin, isoginkgetin and analogues thereof, 2-((7methoxy-4-methylquinazolin-2-yl)amino)-5,6-dimethylpyrimidin-4(3H)-one, and bovine papillomavirus type 1 (BPV-1) exonic splicing suppressor (ESS), N-[2-(1-Piperidinyl)-5-(trifluoromethyl) phenyl]-4-pyridinecarboxamide (SRPIN340), wherein the therapeutically synergistic amounts of at least one a PIM kinase inhibitor that exhibits changes and/or disruption of mRNA splicing in combination with a compound that modulates/inhibits splicing activity of an RNA splicing factor has a molar ratio within the range from about 20:0.001 to 0.01:20 and wherein the cancer is selected from the group consisting of: bone cancer, gynecological cancer, breast cancer, hematological malignancy, skin cancer, liver cancer, kidney cancer, pancreatic cancer, brain cancer, lung cancer, and prostate cancer and wherein the combination has a therapeutic effect on cancerous tissue which is greater than the sum of the individual therapeutic effects of the individual compounds.

2. The composition of claim 1, wherein the RNA splicing factor is a member selected from the group consisting of:
SRSF1_HUMAN Serine/arginine-rich splicing factor 1 OS=Homo sapiens GN=SRSF1 PE=1 SV=2;
SRSF5_HUMAN Serine/arginine-rich splicing factor 5 OS=Homo sapiens GN=SRSF5 PE=1 SV=1;
SRSF6_HUMAN Serine/arginine-rich splicing factor 6 OS=Homo sapiens GN=SRSF6 PE=1 SV=2;
SRSF7_HUMAN Serine/arginine-rich splicing factor 7 OS=Homo sapiens GN=SRSF7 PE=1 SV=1;
SRS1O_HUMAN Serine/arginine-rich splicing factor 10 OS=Homo sapiens GN=SRSF10 PE=1 SV=1;
U2AF1_HUMAN Splicing factor U2AF 35 kDa subunit OS=Homo sapiens GN=U2AF1 PE=1 SV=3;
CWC22_HUMAN Pre-mRNA-splicing factor CWC22 homolog OS=Homo sapiens GN=CWC22 PE=1 SV=3;
SF3B2_HUMAN Splicing factor 3B subunit 2 OS=Homo sapiens GN=SF3B2 PE=1 SV=2;
SF01 HUMAN Splicing factor 1 OS=Homo sapiens GN=SF1 PE=1 SV=4;
SFR19 HUMAN Splicing factor, arginine/serine-rich 19 OS=Homo sapiens GN=SCAF1 PE=1 SV=3;
PR38A_HUMAN Pre-mRNA-splicing factor 38A OS=Homo sapiens GN=PRPF38A PE=1 SV=1;
SPF45 HUMAN Splicing factor 45 OS=Homo sapiens GN=RBM17 PE=1 SV=1;
SF3A2 HUMAN Splicing factor 3A subunit 2 OS=Homo sapiens GN=SF3A2 PE=1 SV=2;
HNRL2 HUMAN Heterogeneous nuclear ribonucleoprotein U-like protein 2OS=Homo sapiens GN=HNRNPUL2 PE=1 SV=1;
HNRPC HUMAN Heterogeneous nuclear ribonucleoproteins C1/C2 OS=Homo sapiens GN=HNRNPC PE=1 SV=4;
ROA1 HUMAN Heterogeneous nuclear ribonucleoprotein A1 OS=Homo sapiens GN=HNRNPA1 PE=1 SV=5;
ROA2 HUMAN Heterogeneous nuclear ribonucleoproteins A2/B1 OS=Homo sapiens GN=HNRNPA2B1 PE=1 SV=2;
RA1L2_HUMAN Heterogeneous nuclear ribonucleoprotein A1-like 2 OS=Homo sapiens GN=HNRNPA1L2 PE=2 SV=2;
ROA3 HUMAN Heterogeneous nuclear ribonucleoprotein A3 OS=Homo sapiens GN=HNRNPA3 PE=1 SV=2;
HNRPM HUMAN Heterogeneous nuclear ribonucleoprotein M OS=Homo sapiens GN=HNRNPM PE=1 SV=3;
HNRDL_HUMAN Heterogeneous nuclear ribonucleoprotein D-like OS=Homo sapiens GN=HNRNPDL PE=1 SV=3;
ROAO_HUMAN Heterogeneous nuclear ribonucleoprotein A/B OS=Homo sapiens GN=HNRNPAB PE=1 SV=2;
ROAA HUMAN Heterogeneous nuclear ribonucleoprotein A/B OS=Homo sapiens GN=HNRNPAB PE=1 SV=2;
HNRPK HUMAN Heterogeneous nuclear ribonucleoprotein K OS=Homo sapiens GN=HNRNPK PE=1 SV=1;

HNRPL HUMAN Heterogeneous nuclear ribonucleoprotein L OS=Homo sapiens GN=HNRNPL PE=1 SV=2;

ROA3_HUMAN Heterogeneous nuclear ribonucleoprotein A3 OS=Homo sapiens GN=HNRNPA3 PE=1 SV=2;

ROAO_HUMAN Heterogeneous nuclear ribonucleoprotein AO OS=Homo sapiens GN=HNRNPAO PE=1 SV=1; and HNRPU HUMAN Heterogeneous nuclear ribonucleoprotein U OS=Homo sapiens GN=HNRNPU PE=1 SV=6.

3. The composition of claim 1, wherein the PIM kinase inhibitor is a dual PIM-1/PIM-2 inhibitor.

4. The composition of claim 1, wherein the PIM kinase inhibitor is a pan-PIM inhibitor.

5. The composition of claim 1, wherein the hematological malignancy is selected from the group consisting of: acute lymphoblastic leukemia (ALL), acute myeloid leukemia (AML), chronic lymphocytic leukemia (CLL), chronic myelogenous leukemia (CML), hairy cell leukemia, AIDS-related lymphoma, B-cell lymphoma, cutaneous T-cell lymphoma, Hodgkin lymphoma, non-Hodgkin lymphoma, mycosis fungoides, primary central nervous system lymphoma, Sezary syndrome, Waldenstrom macroglobulinemia, chronic myeloproliferative disorders, Langerhans cell histiocytosis, multiple myeloma, plasma cell neoplasms, myelodysplastic syndromes, myelodysplastic neoplasms, and myeloproliferative neoplasms.

6. A synergistically therapeutic composition for treating cancer and/or reducing proliferation of cancer cells, wherein the synergistically therapeutic composition comprises a combination of a PIM kinase modulator/inhibitor that exhibits changes of mRNA splicing in combination with a compound that modulates and/or inhibits splicing activity of an RNA splicing factor, wherein the PIM kinase inhibitor is a pan-PIM inhibitor and wherein the compound that modulates and/or inhibits splicing activity of a RNA splicing factor is natural product of *Pseudomonas* sp. number 2663 (FR901464), natural products from *Streptomyces platensis* Mer-11107, pladienolide B, herboxidien, trichostatin, isoginkgetin and analogues thereof, 2-((7methoxy-4-methylquinazolin-2-yl)amino)-5,6-dimethylpyrimidin-4(3H)-one, and bovine papillomavirus type 1 (BPV-1) exonic splicing suppressor (ESS), N-[2-(1-Piperidinyl)-5-(trifluoromethyl)phenyl]-4-pyridinecarboxamide (SRPIN340), wherein the cancer is selected from the group consisting of: bone cancer, gynecological cancer, breast cancer, hematological malignancy, skin cancer, liver cancer, kidney cancer, pancreatic cancer, brain cancer, lung cancer, and prostate cancer and wherein the combination is administered concurrently or sequentially to provide a synergistic effect.

* * * * *